(12) United States Patent
Thomas et al.

(10) Patent No.: US 7,135,335 B2
(45) Date of Patent: Nov. 14, 2006

(54) METHOD FOR SEPARATING CELLS USING IMMUNOROSETTES

(75) Inventors: Terry E. Thomas, Vancouver (CA); Carrie E. Peters, Vancouver (CA); Peter M. Lansdorp, Vancouver (CA)

(73) Assignee: StemCell Technologies Inc., Vancouver (CA)

( * ) Notice: Subject to any disclaimer, the term of this patent is extended or adjusted under 35 U.S.C. 154(b) by 599 days.

(21) Appl. No.: 10/310,990

(22) Filed: Dec. 6, 2002

(65) Prior Publication Data
US 2003/0185817 A1    Oct. 2, 2003

Related U.S. Application Data

(63) Continuation-in-part of application No. 09/822,823, filed on Apr. 2, 2001, now Pat. No. 6,750,326, which is a continuation-in-part of application No. 09/579,463, filed on May 26, 2000, now Pat. No. 6,448,075.

(60) Provisional application No. 60/203,477, filed on May 11, 2000, provisional application No. 60/193,371, filed on Mar. 31, 2000, provisional application No. 60/136,770, filed on May 28, 1999.

(51) Int. Cl.
C07K 16/28 (2006.01)
C12N 5/06 (2006.01)

(52) U.S. Cl. ............ 435/325; 422/102; 435/2; 435/371; 435/372; 435/288.1; 436/819; 530/387.3; 530/388.7

(58) Field of Classification Search ........ 422/102; 435/2, 7.24, 7.25, 325, 371, 372, 288.1; 436/520, 436/814; 530/387.3, 388.7
See application file for complete search history.

(56) References Cited

U.S. PATENT DOCUMENTS

| | | | |
|---|---|---|---|
| 4,004,975 | A | 1/1977 | Lionetti et al. |
| 4,111,199 | A | 9/1978 | Djerassi |
| 4,190,535 | A | 2/1980 | Luderer et al. |
| 4,255,256 | A | 3/1981 | Ferrante et al. |
| 4,751,001 | A | 6/1988 | Saunders |
| 4,818,418 | A | 4/1989 | Saunders |
| 4,868,109 | A | 9/1989 | Lansdorp |
| 4,927,749 | A | 5/1990 | Dorn |
| 4,927,750 | A | 5/1990 | Dorn |
| 5,053,134 | A | 10/1991 | Luderer et al. |
| 5,086,002 | A | 2/1992 | Hillyard et al. |
| 5,397,479 | A | 3/1995 | Kass et al. |

(Continued)

FOREIGN PATENT DOCUMENTS

EP    0 578631 B1    7/1996

(Continued)

OTHER PUBLICATIONS

Bertolini, F. et al., Haematologica, 82(2): 220-238 (1997).

(Continued)

*Primary Examiner*—David Saunders
(74) *Attorney, Agent, or Firm*—Bereskin & Parr; Micheline Gravelle (57) ABSTRACT

The present invention relates to methods for separating cells using immunorosettes. The method involves contacting a sample containing nucleated cells and red blood cells with an antibody composition which allows immunorosettes of the nucleated cells and the red blood cells to form. The antibody composition preferably contains bifunctional antibodies or tetrameric antibody complexes.

14 Claims, 1 Drawing Sheet

U.S. PATENT DOCUMENTS

| | | | |
|---|---|---|---|
| 5,470,570 | A | 11/1995 | Taylor et al. |
| 5,474,687 | A | 12/1995 | Van Vlasselaer |
| 5,482,829 | A | 1/1996 | Kass et al. |
| 5,489,386 | A | 2/1996 | Saunders |
| 5,576,185 | A | 11/1996 | Coulter et al. |
| 5,646,004 | A | 7/1997 | Van Vlasselaer |
| 5,648,223 | A | 7/1997 | Van Vlasselaer |
| 5,676,849 | A | 10/1997 | Sammons et al. |
| 5,840,502 | A | 11/1998 | Van Vlasselaer |
| 5,877,299 | A | 3/1999 | Thomas et al. |
| 6,117,985 | A | 9/2000 | Thomas et al. |
| 6,306,575 | B1 | 10/2001 | Thomas et al. |
| 6,448,075 | B1 * | 9/2002 | Thomas et al. ............ 435/325 |

FOREIGN PATENT DOCUMENTS

WO   WO 00/73794 A2 *   12/2000

OTHER PUBLICATIONS

Bildirici and Rickwood, 2000, J. Immunol. Meth. 240: 93-99.
Bildirici and Rickwood, 2001, J. Immunol. Meth. 252: 57-62.
BioErgonomics, Inc. Fall 1997-Spring 1998 Catalogue, p. 6 PrepaCyte-SC™.
Boyum, A, 1968, Scand. J. Clin. Lab. Invest., vol. 21 Suppl. 97, 9-29.
Boyum, A, 1968, Scand. J. Clin. Lab. Invest., vol. 21 Suppl. 97, 31-50.
Boyum, A, 1968, Scand. J. Clin. Lab. Invest., vol. 21 Suppl. 97, 51-76.
Braun et al., N. Engl. J. Med., 342:525:533 (2000).
Clarke et al., Blood, 96(11), pt.1: 766a-767a (2000).
Collins et al., Journal of Immunological Methods. 243:125-145 (2000).
deWynter, E.A. et al., 1995, Stem Cells, vol. 13:524-532.
Firat et al., 1998, Bone Marrow Transplantation, vol. 21:933-938.
Hirn-Scavennec et al., Transplantation, 46 (4): 558-563 (1988).
Hoogerbrugge, P.M. et al., Blood, 94:142a, 1999.
Fisker, S., K. Kudahl, O. Sonne, 1990, J. Immunol. Meth., vol. 133, 31-38.
Ford, T.C. and D. Rickwood, 1990, J. Immunol. Meth., vol. 134, 237-241.
Janeway Jr. et al., Immunobiology: The Immune System in Health and Disease, 3rd ed.: A1-A10 (1997).
Kenyon et al., Rapid Enrichment of Hematopoietic Stem Cells from Human Vertebral Body Marrow, 3rd Intl Congress of Cell Transplant Society Abstracts.
Labuguen et al., Immunology Letters, 32: 175-180 (1992).
Lillevang, S.T., P. Toft, B. Nielsen, 1994, J. Immunol. Meth., vol. 169, 137-138.
Noble, P.B et al., 1968, Blood, vol. 31(1), 66-73.
Patel et al., 1993, J. Immunol. Meth., 163,:241-251.
Patel et al., 1995, Clinica Chimica Acta 240: 187-193.
Patel and Rickwood, 1995, J. Immunol. Meth. 184: 71-80.
Peters et al., FASEB Journal, 14(6): A989 (2000).
Peters et al., Blood, 96(11), pt. 2: 323b (2000).
Pertoft, H. et al., 1977, Exp. Cell Res., vol. 110, 449-457.
Ruijs, W.P.M., F. Preijers, A. Schattenberg, 2000, ISHAGE proceedings, 24.
Shpall, E.J., et al. 1994, J. of Clinical Oncology 12:28-36.
Schreiner, T. et al., Transfus. Sci., 17:637-642, 1996.
Skoog and Beck, Blood, 11:436, 1956.
Slaper-Cortenbach, Ineke C.M., et al., Experimental Hematology, 18:49-54, 1990.
Slaper-Cortenbach, Ineke C.M., et al., Progress in Clinical and Biological Research, 333:337-344, 1990.
Slaper-Cortenbach, Ineke C.M., et al., Progress in Clinical and Biological Research, 377:147-162, 1992.
Slaper-Cortenbach, Ineke C.M., et al., Rheumatology, 38:751-754, 1999.
StemCell Technologies, 1999/2000 Catalogue supplement.
StemCell Technologies Website: Technical Bulletin for Density Gradient Separation with RosetteSep-TM DM-L; http://www.stemcell.stemmcell/ pdfs/ pfd_bulletins / rsdml_tb.pdf.
Thomas, T.E., 1994, Cancer Research, Therapy and Control 4(2): 119-128.
Ulmer, A.J., H.D. Flad, 1979, J. Immunol. Meth., vol. 30, 1-10.
Wintrobe, M., Clinical Hematology (1975) ed. pp. 125-127.
Woodside et al., Blood, 96(11), pt. 1: 775a (2000).
Vaughan et al., 1990, Proc. Am. Soc. Clin. Oncol. 9:9.
Vervoordeldonk, Susan F. et al., Advances in Bone Marrow Purging and Processing: Fourth International Symposium, 601-609, 1994.
Vervoordeldonk, Susan F. et al., Journal of Hematotherapy, 6:495-500, 1997.
Zwerner et al., Journal of Immunological Methods, 198: 199-202 (1996).

* cited by examiner

FIGURE 1

METHOD FOR SEPARATING CELLS USING IMMUNOROSETTES

This application is a continuation-in-part of U.S. application Ser. No. 09/822,823 filed Apr. 2, 2001 (now U.S. Pat. No. 6,750,326) which is a continuation-in-part of U.S. application Ser. No. 09/579,463 filed May 26, 2000 (now U.S. Pat. No. 6,448,075) which claim benefit from U.S. provisional application Ser. No. 60/203,477 filed on May 11, 2000; U.S. provisional application Ser. No. 60/193,371 filed on Mar. 31, 2000 (now abandoned); and U.S. provisional application No. 60/136,770 filed on May 28, 1999 (now abandoned), all of which are incorporated herein by reference in their entirety.

FIELD OF THE INVENTION

The present invention relates to methods for separating cells using immunorosettes. The invention includes novel antibody compositions for use in the method of the invention.

BACKGROUND OF THE INVENTION

In many applications it is desirable to enrich or, alternatively, deplete certain cell populations in a biological sample. The fields of hematology, immunology and oncology rely on samples of peripheral blood and cell suspensions from related tissues such as bone marrow, spleen, thymus and fetal liver. The separation of specific cell types from these heterogeneous samples is key to research in these fields and to the diagnostics and therapy for certain malignancies and immune/hematopoietic disorders.

Purified populations of immune cells such as T cells and antigen presenting cells are necessary for the study of immune function and are used in immunotherapy. Investigation of the cellular, molecular and biochemical processes require analysis of certain cell types in isolation. Numerous techniques have been used to isolate T cell subsets, B cells, basophils, NK cells and dendritic cells.

The isolation of hematopoietic stem cells has also been an area of great interest. Pure populations of stem cells will facilitate studies of hematopoiesis and transplantation of hematopoietic cells from peripheral blood and/or bone marrow is increasingly used in combination with high-dose chemo- and/or radiotherapy for the treatment of a variety of disorders including malignant, nonmalignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogenic grafts, and tumor cells in autologous transplants that may cause recurrence of the malignant growth. It is also important to debulk the graft by removing unnecessary cells and thus reducing the volume of cyropreservant to be infused.

In certain instances it is desirable to remove or deplete tumor cells from a biological sample, for example in bone marrow transplants. Epithelial cancers of the bronchi, mammary ducts and the gastrointestinal and urogenital tracts represent a major type of solid tumors seen today. Micrometastatic tumor cell migration is thought to be an important prognostic factor for patients with epithelial cancer (Braun et al., 2000; Vaughan et al., 1990). The ability to detect such metastatic cells is limited by the effectiveness of tissue or fluid sampling and the sensitivity of tumor detection methods. A technique to enrich circulating epithelial tumor cells in blood samples would increase the ability to detect metastatic disease and facilitate the study of such rare cells and the determination of the biological changes which enable spread of disease.

Hematopoietic cells and immune cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic approaches to separating cell populations from blood and related cell suspensions using monoclonal antibodies. They differ in whether it is the desired or undesired cells which are distinguished/labelled with the antibody(s).

In positive selection techniques the desired cells are labelled with antibodies and removed from the remaining unlabelled/unwanted cells. In negative selection, the unwanted cells are labelled and removed. Antibody/complement treatment and the use of immunotoxins are negative selection techniques, but FACS sorting and most batch wise immunoadsorption techniques can be adapted to both positive and negative selection. In immunoadsorption techniques cells are selected with monoclonal antibodies and preferentially bound to a surface which can be removed from the remainder of the cells e.g. column of beads, flasks, magnetic particles. Immunoadsorption techniques have won favour clinically and in research because they maintain the high specificity of targeting cells with monoclonal antibodies, but unlike FACSorting, they can be scaled up to deal directly with the large numbers of cells in a clinical harvest and they avoid the dangers of using cytotoxic reagents such as immunotoxins, and complement. They do however, require the use of a "device" or cell separation surface such as a column of beads, panning flask or magnet.

Current techniques for the isolation of hematopoietic stem cells, immune cells and circulating epithelial tumor cells all involve an initial step to remove red cells then antibody mediated adherence to a device or artificial particle. (Firat et al., 1988; de Wynter et al., 1975; Shpall et al., 1994; Thomas et al., 1994; Miltenyi Biotec Inc., Gladbach, Germany) In the case of positive selection there is yet another step; removal of the cells from the device or particle. All these multiple steps require time and incur cell loss. Slaper-Cortenbach et al. (1990) describes a method for purging bone marrow of common acute leukemic (cALL) cells using immunorosetting. The method requires that the erythrocytes are first removed from the bone marrow sample and are labelled with antibodies that bind to the cALL cells. The labelled erythrocytes are then added back to the sample where the cALL cells are immunorosetted. The depletion method works best when followed by an additional step of complement mediated lysis of the cALL cells.

Time dependent sedimentation has been used to deplete red cells from peripheral blood. Many agents have been used to accelerate the sedimentation of red cells by causing the red cells to aggregate or agglutinate. The orientation of red cells in such aggregates has been termed "rouleaux" (Roboredo et al 2000; Wintrobe ed., Clinical Hematology, 1975, Lea and Febiger)

Density Separations are commonly used to isolate peripheral blood mononuclear cells from granulocytes and erythrocytes. Ficoll Hypaque (Amersham Pharmacia Biotech AB, Uppsala Sweden) is the most popular density solution used for this application. Ficoll Hypaque consists of an aggregating agent (polysucrose) in a density solution (diatrizoate sodium). In a Ficoll Hypaque density separation whole blood is layered over the Ficoll Hypaque solution, and then centrifuged. The erythrocytes and granulocytes settle to the cell pellet and the mononuclear cells remain at the Ficoll Hypaque plasma interface.

The success of the Ficoll Hypaque density separation technique relies on the difference in density between mononuclear cells and granulocytes. If whole blood is stored for more than 24 hours the granulocytes change density and will not pellet with the red cells. Suspensions of pure mononuclear cells cannot be obtained from stored blood or samples with altered cell density in a single density separation.

In view of the foregoing, there is a need in the art to provide novel methods for separating desired cells or removing unwanted cells from biological samples.

SUMMARY OF THE INVENTION

The present inventors have developed a method for separating cells by immunorosetting the cells with red blood cells or erythrocytes already existing in the sample. The method of the invention is a much simpler yet equally efficient immunoaffinity technique as compared to the prior art methods. There is no "device" or need for an artificial separation surface (e.g., magnetic particles, affinity column) not normally present in the cell suspension. There is no need to first remove the erythrocytes from the sample and to then re-introduce them once they have been labelled with antibodies. Specific cell types are cross-linked to autologous erythrocytes found within the sample and subsequent aggregates or rosettes are then removed by sedimentation or centrifugation.

Accordingly, in one embodiment, the present invention provides a method of separating nucleated cells from a sample comprising the nucleated cells and erythrocytes comprising:

(1) contacting the sample with an antibody composition comprising (a) at least one antibody that binds to an antigen on the nucleated cells to be separated linked, either directly or indirectly, to (b) at least one antibody that binds to the erythrocytes, under conditions to allow immunorosettes of the nucleated cells and the erythrocytes to form; and (2) removing the immunorosettes from the sample.

The method can be used in both positive and negative selection protocols. The method can be used on any sample that contains red blood cells including whole blood, bone marrow, fetal liver, cord blood, buffy coat suspensions, pleural and peritoneal effusion and samples of thymocytes and splenocytes.

BRIEF DESCRIPTION OF THE DRAWINGS

The invention will now be described in relation to the drawings in which.

DETAILED DESCRIPTION OF THE INVENTION

I. Method of the Invention

As hereinbefore mentioned, the present invention relates to a method for separating cells by immunorosetting the cells with red blood cells.

In its broadest aspect, the present invention provides a method of separating nucleated cells from a sample comprising the nucleated cells and erythrocytes comprising:

(1) contacting the sample with an antibody composition comprising (a) at least one antibody that binds to an antigen on the nucleated cells to be separated linked, either directly or indirectly, to (b) at least one antibody that binds to the erythrocytes, under conditions to allow immunorosettes of the nucleated cells and the erythrocytes to form; and (2) removing the immunorosettes from the sample.

The term "immunorosette" as used herein means an antibody mediated "rosette" formation.

The term "rosette" includes forming an aggregate, agglutinate or rouleaux of red blood cells or erythrocytes.

The term "binds" as used herein includes both specific and non-specific binding of an antibody to an antigen or cell. "Specific binding" means that the antibody has been generated to specifically bind to the antigen through its variable region. "Non specific binding" means that the antibody binds to the antigen or cell through non specific means such as the binding of the Fc portion of an antibody to an Fc receptor.

The method can be used in both positive and negative selection protocols. In positive selection, the desired cells are rosetted. In such an embodiment, the method would further include the step of lysing the red blood cells in the immunorosettes and separating the desired cells. Accordingly, in a positive selection method the antibody composition will contain (a) at least one antibody specific for the nucleated cells that one wishes to obtain or separate from the sample.

Preferably, the method of the invention is used in a negative selection protocol. In negative selection, the desired cells are not immunorosetted and would be remaining in the sample once the immunorosettes have been removed. In a negative selection method, the antibody composition will contain (a) at least one antibody specific for the cells that one wishes to remove from the sample. Accordingly, the present invention provides a negative selection method for enriching and recovering desired cells in a sample containing the desired cells, erythrocytes and undesired cells comprising:

(1) contacting the sample with an antibody composition comprising (a) at least one antibody that binds to an antigen on the undesired cells linked, either directly or indirectly, to (b) at least one antibody that binds to the erythrocytes, under conditions to allow immunorosettes of the undesired cells and the erythrocytes to form; and (2) separating the immunorosettes from the remainder of the sample to obtain a sample enriched in the desired cells.

The immunorosettes between the erythrocytes and the unwanted cells formed in step (1) can be separated from the desired cells using a variety of techniques. Most typically these techniques would include sedimentation in response to gravity (1×g) or centrifugal force created by centrifuging the sample and density separation with either a continuous or discontinuous density gradient.

In one embodiment, the sample, containing the immunorosettes, is layered over a buoyant density solution (such as Ficoll Hypaque) and centrifuged. The immunorosettes pellet and the desired cells remain at the interface between the buoyant density solution and the sample. The desired cells are then removed from the interface for further use. Manual recovery of the cells from this interface requires precision of movement to avoid mixing the layers of density solution. Specialized tubes or containers are available to physically separate the lower layer of cells or cell pellet from the upper layers and allow simple recovery of the cells at the interface layer by decanting or pouring off. Examples of such tubes are described in Table 20. In one embodiment, the sample is layered over a buoyant density solution in a specialized container designed to physically separate layers of solution, either before or after step (1). The sample in the container is centrifuged and the immunorosettes pellet and the desired cells remain at the interface between the buoyant density solution and the sample. The cells at the interface layer are recovered by decanting or pouring of the solution in the top section of the container.

Accordingly, the present invention includes the use of a specialized container to separate the immunorosettes from the sample. The "specialized container" can be any container, preferably a tube, that allows the immunorosettes to be physically separated from the rest of the sample. The container will preferably contain an insert that forms a barrier between the sedimented immunorosettes and the sample. The insert can be a gel, a plug, screen or funnel.

In a specific embodiment, the specialized container is an evacuated blood collection tube containing anti-coagulant, buoyant density medium and a thixotropic gel; such as a Vacutainer CPT tube.

In another embodiment, the sample is mixed with an aggregating agent and the antibody composition in step (1). The immunorosettes sediment and the desired cells remain in suspension and are removed for further use. The "aggregating agent" can be any agent that can accelerate the sedimentation of red cells by causing the red cells to aggregate or agglutinate. Examples of aggregating agents that can be used in the method of the invention are listed in Table 19. In a specific embodiment, the aggregating agent is dextran or hetastarch which is demonstrated in Example 3. The aggregating agent can be added before, after or simultaneously with the antibody composition.

In a further embodiment, the sample containing the immunorosettes obtained in step (1) is allowed to sediment with or without the aid of centrifugation or Counter Flow Elutriation. The desired cells remain in suspension and are removed for further use. Manual recovery of the solution above the cell pellet requires precision of movement to avoid re-suspension of the cells in the pellet. Specialized tubes or containers are available to physically separate the lower layer of cells or cell pellet from the upper layers and allow simple recovery of the cells in suspension by decanting or pouring off. Examples of such tubes are described in Table 20. In one embodiment, the sample is placed in a specialized container designed to physically separate layers of solution (examples of specialized containers given in Table 20) either before or after contacting with the aggregating agent and the antibody composition. The immunorosettes sediment out and the desired cells remain in suspension in the top section of the container. The desired cells are recovered by decanting or pouring of the solution in the top section of the container.

The antibody compositions for use in the present invention are described in greater detail below.

The method of the invention may be used in the processing of biological samples that contain erythrocytes including blood (in particular, cord blood and whole blood) bone marrow, fetal liver, buffy coat suspensions, pleural and peritoneal effusions and suspensions of thymocytes and splenocytes. Surprisingly, the inventors have found that the method can be used to remove cells directly from whole blood or whole bone marrow without prior processing. This offers a significant advantage of the method of the invention over the prior art methods. In particular, the erythrocytes do not have to be removed, labelled and added back to the sample.

The method of the invention can be used to prepare enriched samples of any cell type including, but not limited to, T cells, B cells, NK cells, dendritic cells, monocytes, basophils, mast cells, progenitor cells, stem cells and tumor cells.

In one embodiment, the method of the invention can be used to enrich for non-hematopoietic cells including normal cells as well as non-hematopoietic tumor cells. Examples of normal non-hematopoietic cells include epithelial cells, endothelial cells, mesenchymal cells or precursors thereof.

In yet another embodiment, the method of the invention can be used to separate non-hematopoietic tumor cells, such as non-hematopoietic metastatic tumor cells from a sample. The method is useful in the detection of non-hematopoietic tumor cells from blood, bone marrow, and peritoneal and pleural effusions of patients to aid in the diagnosis and detection of metastatic disease, monitoring the progression of metastatic disease, or monitoring the efficacy of a treatment.

In another embodiment, the method of the invention can be used to prepare hematopoietic progenitor and stem cell preparations from bone marrow samples. For example, the method of the invention may be used in a negative selection protocol to deplete or purge B and T lymphocytes, monocytes, NK cells, granulocytes, and/or tumor cells from samples to prepare hematopoietic progenitor and stem cell preparations for use in transplantation as well as other therapeutic methods that are readily apparent to those of skill in the art. For example, bone marrow or blood can be harvested from a donor in the case of an allogenic transplant and enriched for progenitor and stem cells by the method described herein. Using negative selection the human hematopoietic progenitor and stem cells in the preparation are not coated with antibodies, or modified making them highly suitable for transplantation and other therapeutic uses that are readily apparent to those skilled in the art.

In another embodiment, the method of the invention can be used to isolate and recover mature dendritic cells and their precursors from blood. Dendritic cells have many useful applications including as antigen presenting cells capable of activating T cells both in vitro and in vivo. As an example, dendritic cells can be loaded (pulsed) in vitro with a tumor antigen and injected in vivo to induce an anti-tumor T cell response.

In a further embodiment, the method of the invention may also be used to prepare a cell preparation from samples such as blood and bone marrow, which is enriched in a selected differentiated cell type such as T-cells, B-cells, NK cells, monocytes, dendritic cells, basophils and plasma cells. This will enable studies of specific cell to cell interactions including growth factor production and responses to growth factors. It will also allow genetic, molecular and biochemical analysis of specific cells types. Cell preparations enriched in NK cells, dendritic cells and T-cells may also be used in immune therapy against certain malignancies.

II. Antibody Compositions

The invention includes the antibody compositions for use in the method of the present invention. The antibody composition will contain (a) at least one antibody that binds to an antigen on nucleated cells linked, either directly or indirectly, to (b) at least one antibody that binds to an antigen on erythrocytes.

The term "at least one antibody" means that the antibody composition includes at least one type of antibody (as opposed to at least one antibody molecule). One type of antibody means an antibody that binds to a particular antigen. For example, antibodies that bind to the antigen CD2 are considered one type of antibody. Preferably, the antibody compositions of the invention contain (a) more than one antibody type that binds to nucleated cells.

The two antibodies (a) and (b) may be directly linked by preparing bifunctional or bispecific antibodies. The two antibodies (a) and (b) may be indirectly linked for example, by preparing tetrameric antibody complexes. All of these are described hereinafter.

In one aspect, the antibody specific for the nucleated cells is linked directly to the antibody specific for the erythrocytes. In one embodiment, the antibody composition of the present invention contains bifunctional antibodies comprising at least one antibody specific for the nucleated cells linked directly to (b) at least one antibody specific for the erythrocytes. Bifunctional antibodies may be prepared by chemically coupling one antibody to the other, for example by using N-succinimidyl-3-(2-pyridyldithio) propionate (SPDP).

In another embodiment, the antibody composition contains bispecific antibodies. Bispecific antibodies contain a variable region of an antibody specific for erythrocytes and a variable region specific for at least one antigen on the surface of the nucleated cells to be separated. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

In another aspect, the antibody composition of the present invention comprises (a) at least one antibody specific for a nucleated cell type indirectly linked to (b) at least one antibody specific for the erythrocyte. By "indirectly linked" it is meant that antibody (a) and antibody (b) are not directly covalently linked to each other but are attached through a linking moiety such as an immunological complex, molecule with multiple binding sites, substituted macromolecule or physical substrate such as particles or other prepared surfaces. In a preferred embodiment, the antibody to the nucleated cell type is indirectly linked to the antibody specific for the erythrocytes by preparing a tetrameric antibody complex. A tetrameric antibody complex may be prepared by mixing a first monoclonal antibody which is capable of binding to the erythrocytes, and a second monoclonal antibody capable of binding the nucleated cells to be separated. The first and second monoclonal antibody are from a first animal species. The first and second antibody are reacted with approximately an equimolar amount of monoclonal antibodies of a second animal species which are directed against the Fc-fragments of the antibodies of the first animal species. The first and second antibody may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

Preferably, the antibody specific for the erythrocytes is anti-glycophorin A. The anti-glycophorin A antibodies contained in the antibody composition of the invention are used to bind the erythrocytes. Examples of monoclonal antibodies specific for glycophorin A are 10F7MN (U.S. Pat. No. 4,752,582, Cell lines: ATCC accession numbers HB-8162), and D2.10 (Immunotech, Marseille, France).

Preferably, the antibody specific for the nucleated cells is a combination of antibodies. The combination of antibodies may be specific for a number of cell types so that many cell types may be removed from the sample. When using a combination of antibodies, each antibody will be linked (either directly or indirectly) to an antibody specific for erythrocytes.

Figure 1:
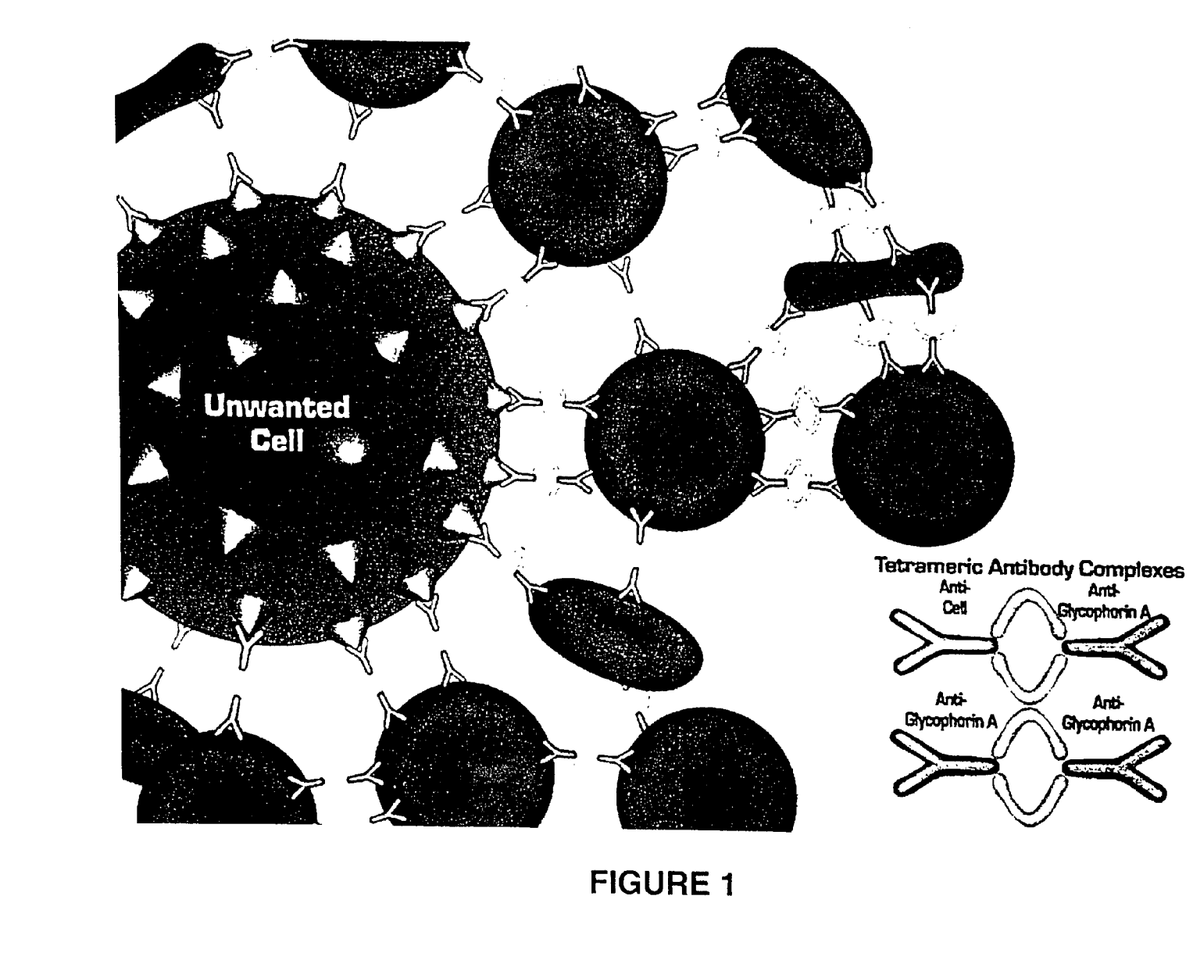
FIG. 1 is a schematic diagram of a rosette of erythrocytes formed around an unwanted nucleated cell using tetrameric antibody complexes.

In a preferred embodiment, the antibody composition is a tetrameric complex comprising (a) anti-glycophorin A antibodies to bind the erythrocytes, (b) an antibody that binds to a nucleated cell type that one wishes to immunorosette and (c) antibodies that bind the Fc portion of both (a) and (b), optionally F(ab')$_2$ antibody fragments. The molar ratio of (a):(b):(c) may be approximately 1:3:4. When several types of cells are to be separated, complexes are made with several anti-nucleated cell antibodies (b). The complexes may then be mixed together to form an antibody composition for use in the method of the invention. FIG. 1 is a schematic diagram of a rosette formed by tetrameric antibody complexes.

Within the context of the present invention, antibodies are understood to include monoclonal antibodies and polyclonal antibodies, antibody fragments (e.g., Fab, and F(ab')$_2$), chimeric antibodies, bifunctional or bispecific antibodies and tetrameric antibody complexes. Antibodies are understood to be reactive against a selected antigen on the surface of a nucleated cell or erythrocyte if they bind with an appropriate affinity (association constant), e.g. greater than or equal to $10^7$ M$^{-1}$.

Monoclonal antibodies are preferably used in the antibody compositions of the invention. Monoclonal antibodies specific for selected antigens on the surface of nucleated cells may be readily generated using conventional techniques. For example, monoclonal antibodies may be produced by the hybridoma technique originally developed by Kohler and Milstein 1975 (Nature 256, 495–497; see also U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988). Other techniques may also be utilized to construct monoclonal antibodies (for example, see William D. Huse et al., 1989, "Generation of a Large Combinational Library of the Immunoglobulin Repertoire in Phage Lambda," Science 246:1275–1281, L. Sastry et al., 1989 "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732; Kozbor et al., 1983

Immunol. Today 4, 72 re the human B-cell hybridoma technique; Cole et al. 1985 Monoclonal Antibodies in Cancer Therapy, Allen R. Bliss, Inc., pages 77–96 re the EBV-hybridoma technique to produce human monoclonal antibodies; and see also Michelle Alting-Mees et al., 1990 "Monoclonal Antibody Expression Libraries: A Rapid Alternative to Hybridomas," Strategies in Molecular Biology 3:1–9). Hybridoma cells can be screened immunochemically for production of antibodies specifically reactive with an antigen, and monoclonal antibodies can be isolated.

Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Bifunctional antibodies may be prepared by chemical conjugation, somatic hybridization or genetic engineering techniques.

Chemical conjugation is based on the use of homo- and heterobifunctional reagents with E-amino groups or hinge region thiol groups. Homobifunctional reagents such as 5,5'-Dithiobis(2-nitrobenzoic acid)(DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridyldithio) propionate (SPDP) combine exposed amino groups of antibodies and Fab fragments, regardless of class or isotype (Van Dijk et al., 1989).

Somatic hybridization includes fusion of two established hybridomas generating a quadroma (Milstein and Cuello, 1983) or fusion of one established hybridoma with lymphocytes derived from a mouse immunized with a second antigen generating a trioma (Nolan and Kennedy, 1990). Hybrid hybridomas are selected by making each hybridoma cell line resistant to a specific drug-resistant marker (De Lau et al., 1989), or by labeling each hybridoma with a different fluorochrome and sorting out the heterofluorescent cells (Karawajew et al., 1987).

Genetic engineering involves the use of recombinant DNA based technology to ligate sequences of DNA encoding specific fragments of antibodies into plasmids, and expressing the recombinant protein. Bispecific antibodies can also be made as a single covalent structure by combining two single chains Fv (scFv) fragments using linkers (Winter and Milstein, 1991); as leucine zippers coexpressing sequences derived from the transcription factors fos and jun (Kostelny et al., 1992); as helix-turn-helix coexpressing an interaction domain of p53 (Rheinnecker et al., 1996), or as diabodies (Holliger et al., 1993).

Table 1 provides examples of antibodies to particular human antigens on nucleated cells that may be used in the method of the present invention. The method of the invention may also be used for other species. The choice of the antibody or antibodies to the nucleated cells will depend on the nature of the sample, the choice of the cells to be enriched or depleted and whether the method is a positive or negative selection protocol. In all cases, the antibody (or antibodies) to the nucleated cells to be immunorosetted will be linked, either directly or indirectly, to the antibody specific for the erythrocytes when used in the method of the invention.

The methods and antibody compositions of the invention are preferably used in negative selection protocols to prepare a cell preparation which is enriched for a specific cell type. This is achieved by using antibody compositions which lack antibodies to the specific cell type that you wish to isolate. Accordingly, the present invention provides an antibody composition for enriching and recovering desired cells in a sample containing desired cells, erythrocytes and undesired cells comprising (a) at least one antibody that binds to an antigen on the undesired cells linked to (b) at least one antibody that binds to the erythrocytes. Particular embodiments of the antibody compositions that may be used in negative selection protocols of the invention for human cells are set out in Table 2. This Table provides a list or cocktail of antibodies to particular antigens that can be used as antibody (a) in the above method to enrich for a particular cell type. In most cases, several choices for the essential antibodies are provided as well as several optional antibodies. For example, for enriching for T cells antibody (a) may be a cocktail of antibodies to (1) CD16 and/or CD66b and/or CD11b and/or CD15; (2) CD19 and/or CD20 and/or CD21 and/or CD22 and/or CD24 and/or Ig and/or CD72; and (3) CD36 and/or CD14. The cocktail may optionally include antibodies to CD33 and/or CD56 and/or IgE and/or CD41 and/or CD9. As another example, for enriching for non-hematopoietic cells antibody (a) may be a cocktail of antibodies to (1) CD45 and (2) CD66b and optionally CD36 and/or CD2 and/or CD3 and/or CD14 and/or CD16 and/or CD19 and/or CD38 and/or CD56 and/or CD66e. In a specific embodiment, the antibody composition for enriching for non-hematopoietic tumor cells comprises antibodies to CD45, CD66b and CD36 in addition to the antibodies that can bind the erythrocytes. In addition to the antibody combinations listed in Table 2, one skilled in the art will appreciate that other antibody combinations may be used to enrich for specific cell types such as those described in U.S. Pat. No. 5,877,299 which is incorporated herein by reference. As the invention relates to the preparation of immunorosettes to prepare enriched cell preparations, one skilled in the art will appreciate that other antibodies and antibody combinations may be used.

The methods and antibody compositions of the invention may be used in positive selection protocols to prepare a cell preparation in which the desired cells are immunorosetted. Some examples of antibody combinations useful in positive selection protocols are set out below.

To separate non-hematopoietic tumor cells in a positive selection protocol, the antibody composition includes antibodies specific for non-hematopoietic antigens expressed on tumor cells, such as antibodies against antigens expressed on the surface of breast and lung carcinoma and neuroblastoma cells. The antibodies to the non-hematopoietic antigens expressed on epithelial tumor cells may be obtained from commercial sources (for example as shown in Table 3) or prepared using techniques known in the art.

To separate B cells in a positive selection protocol, the antibody composition contains antibodies against CD24 and/or CD19 and/or CD20 and/or CD22.

To separate T cells in a positive selection protocol, the antibody composition contains antibodies against CD3 and/or CD2 and/or CD5 and/or both CD4 and CD8.

To separate NK cells in a positive selection protocol, the antibody composition contains antibodies against CD56.

To separate granulocytes in a positive selection protocol, the antibody composition contains antibodies against CD16 and/or CD66e and/or CD66b.

To separate monocytes in a positive selection protocol, the antibody composition contains antibodies against CD14.

III. Kits

The present invention also includes kits containing the antibody compositions of the invention for use in separating nucleated cells from a sample according to the method of the invention. The kit will include an antibody composition comprising: (a) at least one antibody that binds to an antigen on the nucleated cells linked to be separated; and (b) at least one antibody that binds to erythrocytes.

Preferably, the antibody specific for the erythrocytes is anti-glycophorin A. Preferably, the antibody specific for the nucleated cells is a combination of antibodies. Examples of combinations of antibodies that can be used are shown in Table 2. The kit will also include instructions for performing the method of the invention and reagents helpful in carrying out the process of the invention.

In one embodiment, the kit will also include an aggregating agent. Examples of aggregating agents listed in Table 19. In a specific embodiment, the aggregating agent is dextran or hetastarch.

In another embodiment, the kit will also include a specialized container. Examples of specialized containers are provided in Table 20.

In a preferred embodiment, the antibody composition is a tetrameric complex comprising: (a) an antibody to bind the erythrocytes (b) an antibody that binds to a nucleated cell type that one wishes to immunorosette and (c) antibodies that bind the Fc portion of both (a) and (b), optionally F(ab')$_2$ antibody fragments. The molar ratio of (a):(b):(c) may be approximately 1:3:4. When several types of cells are to be separated, complexes are made with several anti-nucleated cell antibodies (b). The complexes may then be mixed together to form an antibody composition for use in the method of the invention. FIG. 1 is a schematic diagram of a rosette formed by tetrameric antibody complexes.

In a preferred embodiment, the kit is used in a negative selection process wherein the antibodies to the nucleated cell are directed to antigens on the surface of the cell you wish to remove from the sample. This is described in greater detail hereinabove.

The following non-limiting examples are illustrative of the present invention:

EXAMPLES

Example 1

Preparation of Tetramers

In order to prepare a tetrameric antibody complex for use in the method of the present invention, the following protocol may be used: (a) take 1 mg of antibody specific for cells to be rosetted (e.g. anti-CD2, CD3, CD4, CD8, CD14, CD16, CD19 etc.); (b) add 3 mg anti-Glycophorin A antibody (against red blood cells); mix well (c) then add 4.0 mg of P9 antibody or 2.72 mg of the P9 F(ab')$_2$ antibody fragment. Incubate overnight at 37° C. The P9 antibody binds the Fc portion of the antibodies added in steps (a) and (b) resulting in a tetrameric antibody complex. For more information on the preparation of tetramers see U.S. Pat. No. 4,868,109 to Lansdorp, which is incorporated herein by reference. Tetrameric antibody complexes incorporating different antibodies to antigens expressed on nucleated cells are prepared separately and then mixed.

The antibody compositions are made by combining various tetrameric antibody complexes depending on which cells one wishes to deplete. The concentration of the various tetrameric antibody complexes varies: typically antibodies to antigens expressed on nucleated cells are at 10–30 µg/mL in tetrameric complexes. The composition is then diluted 1/10 into the cells so the final concentrations of each anti nucleated cell antibody in the cell suspensions is 1.0–3.0 µg/mL.

Example 2

Method of Immunorosetting Using Ficoll Hypaque

A negative selection protocol for immunorosetting cells from whole peripheral blood using Ficoll Hypaque is set out below.

1. Add 100 µL antibody composition per mL of whole peripheral blood.
2. Incubate 20 minutes at room temperature.
3. Dilute sample with an equal volume of phosphate buffered saline (PBS)+2% fetal calf serum (FCS) and mix gently.
4. Layer the diluted sample on top of Ficoll Hypaque or layer the Ficoll underneath the diluted sample.
5. Centrifuge for 20 minutes at 1200×g, room temperature, with the brake off.
6. Remove the enriched cells from the Ficoll Hypaque: plasma interface.
7. Wash enriched cells with 5–10x volume of PBS+2% FBS.

Note: For enrichment of monocytes and other adherent cells, add 1 mM EDTA to the sample of whole blood and to all wash/dilution solutions.

Example 3

Method of Immunorosetting Using Hetastarch Sedimentation

A negative selection protocol for immunorosetting cells from whole peripheral blood using hetastarch is set out below. Hetastarch is one of a number of compounds that increases red blood cell sedimentation rates through agglutination.

1. Add 1 mL of 6% hetastarch in saline per 5 mL of blood and mix.
2. Add antibody composition described in Example 1 to whole blood such that each anti-nucleated cell antibody is at a final concentration of 1.0–2.0 µg/mL.
3. Incubate 10 minutes at room temperature.
4. Centrifuge for 5 minutes at 50×g, room temperature.
5. Remove supernatant. This fraction contains the enriched cells.
6. Wash enriched cell fraction with 2–5x volume of PBS+2% fetal bovine serum (FBS).

Example 4

Method of Immunorosetting Using Hetastarch/Iodixanol Mixture

A negative selection protocol for immunorosetting cells from whole peripheral blood is set out below.
1. Add 1 mL of 6% hetastarch in saline per 5 mL of blood and mix.
2. Add 0.6 mL of 60% w/v iodixanol and mix. Iodixanol is one of a number of compounds that increases the aqueous solution density appreciably.
3. Add antibody composition described in Example 1 to whole blood such that each anti-nucleated cell antibody is at a final concentration of 1.0–2.0 μg/mL.
4. Incubate 10 minutes at room temperature.
5. Centrifuge for 5 minutes at 50×g, room temperature.
6. Remove supernatant. This fraction contains the enriched cells.
7. Wash enriched cell fraction with 2–5x volume of PBS+2% FBS.

Example 5

Method of Immunorosetting—Positive Selection

A positive selection protocol for immunorosetting cells from whole peripheral blood is set out below.
1. Set aside 1 mL of blood.
2. Layer 10 mL of blood over Ficoll Hyaque and centrifuge for 20 minutes at 1200×g, room temperature, brake off.
3. Recover the MNC layer at the Ficoll Hypaque:plasma interface, wash with PBS+2% FBS.
4. Count cells and resuspend at $1 \times 10^8$/mL.
5. Measure sample volume, designated volume A.
6. Add 0.2 mL of reserved blood from Step 1.
7. Make up total volume to twice volume A with PBS+2% FBS.
8. Add a tetrameric antibody complex specific to a given antigen at a final concentration of 1.0 μg/mL, the synthesis of which is described in Example 1.
9. Incubate 20 minutes at room temperature.
10. Dilute by a factor of 2 with PBS+2% FBS and layer over Percoll prepared at a density of 1.085 g/mL and an osmolarity of 280 mOsm.
11. Centrifuge for 20 minutes at 1200×g as in Step 2.
12. Discard supernatant and resuspend pellet containing the enriched cells.
13. Lyse red blood cells with ammonium chloride solution and wash with PBS+2% FBS.

Example 6

Enrichment of T Cells—Immunorosetting Using Ficoll

This example demonstrates the enrichment of T cells from whole peripheral blood using the method described in Example 2. A T cell enrichment cocktail of tetrameric antibody complexes containing antibodies against CD16, CD19, CD36 and CD56 was prepared. The results, shown in Table 4, demonstrate that the method of the invention results in 95% purity of T cells with a recovery of close to 50%.

Example 7

Enrichment of CD8+ T Cells—Immunorosetting Using Ficoll

This example demonstrates the enrichment of CD8+ T cells from whole peripheral blood using the method described in Example 2. Two cocktails of tetrameric antibody complexes were tested. One cocktail contained antibodies against CD4, CD16, CD19, CD36 and CD56 the other contained antibodies to CD4, CD16, CD19, CD36, CD56 and IgE. The results, shown in Table 5, demonstrate that the addition of anti IgE to the cocktail improves the purity of CD8+ T cells with no effect on recovery.

Example 8

Enrichment of CD4+ T Cells—Immunorosetting Using Ficoll

This example demonstrates the enrichment of CD4+ T cells from whole peripheral blood using the method described in Example 2. Two CD4 T cell enrichment cocktails of tetrameric antibody complexes were prepared. One cocktail contained antibodies to CD8, CD16, CD19, CD36 and CD56. The other cocktail contained antibodies to CD8, CD16, CD19, CD36, CD56 and IgE. The results, shown in Table 6, demonstrate that the method of the invention results in 93% purity of CD4+ T cells with a recovery of 46% and that addition of anti-IgE to the enrichment cocktail improves the purity of CD4+ T cells.

Example 9

Enrichment of B Cells—Immunorosetting Using Ficoll

This example demonstrates the enrichment of B cells from whole peripheral blood using the method described in Example 2. Two B cell enrichment cocktails of tetrameric antibody complexes were prepared. One cocktail contained antibodies to CD2, CD3, CD16, CD36 and CD56. The other cocktail contained antibodies to CD2, CD3, CD16, CD36, CD56 and IgE. The results, shown in Table 7, demonstrate that the method of the invention results in 88% purity of B cells with a recovery of 43% and that addition of anti-IgE to the cocktail improves the purity of B cells.

Example 10

Enrichment of NK Cells—Immunorosetting Using Ficoll

This example demonstrates the enrichment of NK cells from whole peripheral blood using the method described in Example 2. Two NK cell enrichment cocktails of tetrameric antibody complexes were prepared. One cocktail contained antibodies to CD3, CD4, CD19, CD66b and CD36. The other cocktail contained antibodies to CD3, CD4, CD19, CD66b, CD36 and IgE. The results, shown in Table 8, demonstrate that the method of the invention results in 74% purity of NK cells with a recovery of 44% and that the addition of anti-IgE to the cocktail improves purity but decreases recovery.

Example 11

Enrichment of Progenitors

This example demonstrates the enrichment of progenitor cells from whole umbilical cord blood using the method described in Example 2. Two different cocktails of tetrameric antibody complexes were used;
(a) the progenitor enrichment cocktail containing tetrameric antibody complexes to CD2, CD3, CD14, CD16, CD19, CD24, CD56 and CD66b;
(b) the de-bulking cocktail containing tetrameric antibody complexes to CD2, CD14, CD19 and CD66b.

The results, shown in Table 9, demonstrate that the method of the invention results in 29% purity of CD34+ cells with a recovery of 53% for the extensive progenitor enrichment cocktail and only 5% purity and 45% recovery for the four antibody de-bulking cocktail.

Example 12

Enrichment of Monocytes—Immunorosetting Using Ficoll

This example demonstrates the enrichment of monocytes from whole peripheral blood using the method described in Example 2. Several monocyte enrichment cocktails of tetrameric antibody were prepared (see Table 10). The results shown in Table 10 demonstrate that the method of the invention results in 76% purity of CD14+ cells with 65% recovery of CD14+ cells and that the addition of anti CD8 or anti-IgE improved the purity of monocytes but adding both anti-CD8 and IgE did not have an additive effect.

Example 13

Enrichment of Non-Hematopoietic Tumor Cells

This example demonstrates the enrichment of breast cancer cells from whole peripheral blood using the method described in Example 2. Cells from the CAMA breast cancer cell line were seeded into samples of whole peripheral blood at a frequency of $1/10^3$, $1/10^4$ and $1/10^5$. Four tumor cell enrichment cocktails of tetrameric antibody complexes were prepared. The antibody composition of the cocktails is listed in Table 11. The results, shown in Table 12, demonstrate that the method of the invention results in greater than 2 log enrichment of tumor cells with 20–50% recovery of tumor cells. The more extensive cocktail offers a greater degree of tumor cell enrichment.

The results shown in Table 13, demonstrate the effect of adding anti-CD36 to the tumor enrichment cocktails. Cells from the CAMA breast cancer cell line were seeded into samples of previously frozen peripheral blood mononuclear cell to a concentration of 1.4 CAMA cells per 1,000 nucleated cells. Addition of anti-CD36 to a cocktail containing anti-CD45 and anti-CD66b improved the log enrichment of CAMA cells from 2.6 log to 2.7 log and the purity of CAMA cells from 58% to 77%. However, neither the log enrichment or purity reached the levels attained with the extensive cocktail.

Example 14

T Cell Enrichment—Effect of Substituting Anti-CD14 with Anti-CD36

This example demonstrates the improved T cell enrichment from whole peripheral blood using the method described in Example 2 when the enrichment cocktail is modified by substituting anti-CD36 for anti-CD14. The results in Table 14 show a 24% increase in %purity of CD3+ cells with the antibody substitution.

Example 15

Enrichment of Specific Cell Populations Using Hetastarch Sedimentation

This example demonstrates the enrichment of various cell populations from whole peripheral blood using the method described in Example 3.

A T cell enrichment cocktail of tetrameric antibody complexes containing antibodies against CD16, CD19, CD36 and CD56 was prepared. The method of the invention results in greater than 95% purity of T cells, with a recovery of 60%.

A B cell enrichment cocktail of tetrameric antibody complexes containing antibodies against CD2, CD3, CD16, CD36 and CD56 was prepared. The method of the invention results in 75% purity of B cells, with a recovery of 39%.

A NK cell enrichment cocktail of tetrameric antibody complexes containing antibodies against CD3, CD4, CD19, CD36 and CD66b was prepared. The method of the invention results in 65% purity of NK cells, with a recovery of 27%.

Example 16

Enrichment of Specific Cell Populations Using Hetastarch/ Iodixanol Mixture

This example demonstrates the enrichment of various cell populations from whole peripheral blood using the method described in Example 4. The results, listed in Table 15, are summarized as follows.

A T cell enrichment cocktail of tetrameric antibody complexes containing antibodies against CD16, CD19, CD36 and CD56 was prepared. The method of the invention results in 95% purity of T cells, with a recovery of 61%.

A CD4+ T cell enrichment cocktail of tetrameric antibody complexes containing antibodies against CD8, CD16, CD 19, CD36 and CD56 was prepared. The method of the invention results in 89% purity of CD4+ T cells, with a recovery of 64%.

A CD8+ T cell enrichment cocktail of tetrameric antibody complexes containing antibodies against CD4, CD16, CD 19, CD36 and CD56 was prepared. The method of the invention results in 80% purity of CD8+ T cells, with a recovery of 43%.

A B cell enrichment cocktail of tetrameric antibody complexes containing antibodies against CD2, CD3, CD16, CD36 and CD56 was prepared. The method of the invention results in 84% purity of B cells, with a recovery of 58%.

A NK cell enrichment cocktail of tetrameric antibody complexes containing antibodies against CD3, CD4, CD 19, CD36 and CD66b was prepared. The method of the invention results in 80% purity of NK cells, with a recovery of 50%.

Example 17

Immunorosetting Using Different Layering Media

This example demonstrates that the method of Example 2 can be modified by substituting different media for Ficoll-Hypaque in Step 4. The density of Ficoll was 1.077 g/mL and the osmolarity was approximately 300 mOsm. Percoll and lodixanol solutions were prepared with a density of 1.085 g/mL and an osmolarity of 280 mOsm. A B cell enrichment cocktail containing antibody complexes against CD2, CD3, CD16, CD36 and CD56 was prepared.

The results of B cell enrichments for two separate samples, shown in Table 16, demonstrate that the use of different layering media at a higher density can increase the recovery of B cells without lowering the B cell purity.

Example 18

Purging of T Cells Using Immunorosettes

This example demonstrates the removal of T cells from whole peripheral blood using the method described in Example 2. A T cell purging cocktail of tetrameric antibody complexes to CD3 was prepared. The method of the invention resulted in 2.3 log depletion of CD3+ cells.

Example 19

Purging of B Cells Using Immunorosettes

This example demonstrates the removal of B cells from whole peripheral blood using the method described in Example 2. A B cell purging cocktail of tetrameric antibody complexes to CD19 was prepared. The method of the invention resulted in 3.0 log depletion of CD19+ cells.

Example 20

Purging of Breast Carcinoma Cells Using Immunorosetting

This example demonstrates the removal of breast carcinoma cells from whole peripheral blood seeded with 1–5% CAMA breast carcinoma cells using the method described in Example 2. A purging cocktail of tetrameric antibody complexes containing anti-breast carcinoma antibodies 5E11 and BRST 1 was prepared. The results shown in Table 17 demonstrate the method of the invention results in 1.0–1.4 log depletion of breast carcinoma cells.

Example 21

Removal of Granulocytes from Previously Stored Whole Peripheral Blood

The density of granulocytes in samples of whole peripheral blood decreases with >24 hours of storage. Density separation methods commonly used to remove red cells and granulocytes from fresh whole blood do not efficiently remove granulocytes from stored blood samples. The sedimentation rate of stored granulocytes can be increased to allow efficient removal in a standard Ficoll density separation (1.077 g/mL) by immunorosetting. This example demonstrates the removal of granulocytes from stored (48 hour) whole peripheral blood using the method described in Example 2. A granulocyte depletion cocktail containing tetrameric antibody complexes against CD66b was prepared. The results, shown in Table 18, demonstrate that the method of the invention results in 1.8–2.6 log depletion of granulocytes.

Example 22

Positive Selection of Specific Cell Populations Using Immunorosetting

This example demonstrates the enrichment of CD8+ cells from whole peripheral blood using the positive selection method described in Example 5. A tetrameric antibody complex against CD8 was prepared. The method of the invention results in the enrichment of CD8+ cells as a percentage of the mononuclear cell fraction from 25% in the start to 32% in the pellet.

Example 23

Method of Immunorosetting Using Dendreon Tube

A negative selection protocol for immunorosetting cells from whole peripheral blood using density separation with FicollHypaque and a specialized tube (Dendreon) is set out below. The Dendreon tube is a standard 50 mL polypropylene centrifuge tube with an insert specially designed for use with discontinuous density gradient separation that allows the user to remove the cells at the Ficoll Hypaque:plasma interface by pouring off the tube. The tube is described in U.S. Pat. No. 5,840,502.
1. Add 15 mL of Ficoll-Paque to the Dendreon tube
2. Centrifuge for 5 minutes at 1200 rpm; the Ficoll Hypaque should fill the volume below the insert.
3. Add 50 µL antibody composition per mL of whole peripheral blood
4. Incubate 20 minutes at room temperature.
5. Dilute blood sample with an equal volume of phosphate buffered saline (PBS)+2% fetal bovine serum (FBS) and mix gently.
6. Pour or layer the diluted blood sample on top of Ficoll Hypaque.
7. Centrifuge for 20 minutes at 1200×g, room temperature, with the brake off.
8. Remove the enriched cells from the Ficoll: plasma interface by pipetting off interface or pouring off volume above tube insert.
9. Wash enriched cells with 5–10X volume of PBS+2% FBS.

Example 24

Method of Immunorosetting Using Vacutainer CPT

A negative selection protocol for immunorosetting cells from whole peripheral blood using centrifugation in a specialized blood collection tube ("Vacutainer CPT") is set out below.
1. Add 50 µL antibody composition per mL of whole peripheral blood collected in the Vacutainer CPT.
2. Incubate 20 minutes at room temperature.
3. Centrifuge for 20 minutes at 1600×g, room temperature, with the brake off.
4. Remove the enriched cells from above the gel insert, washing the insert to remove all the enriched cells.
5. Wash enriched cells with 5–10X volume of PBS+2% FBS.

Note: For enrichment of monocytes and other adherent cells, add 1 mM EDTA to the sample of whole blood and to all wash/dilution solutions.

Example 25

Method of Immunorosetting Using Vacutainer CPT and Diluted Peripheral Blood

A negative selection protocol for immunorosetting cells from whole peripheral blood using centrifugation in a specialized blood collection tube ("Vacutainer CPT") is set out below.
1. Collect a maximum of 4 mL of whole peripheral blood in the Vacutainer CPT.
2. Add 50 µL antibody composition per mL of whole peripheral blood collected in the Vacutainer CPT.
3. Incubate 20 minutes at room temperature.

4. Add a volume of PBS+2% FBS equal to the initial blood volume and invert to mix.
5. Centrifuge for 20 minutes at 1600×g, room temperature, with the brake off.
6. Remove the enriched cells from above the gel insert, washing the insert to remove all the enriched cells.
7. Wash enriched cells with 5–10X volume of PBS+2% FBS.

Note: For enrichment of monocytes and other adherent cells, add 1 mM EDTA to the sample of whole blood and to all wash/dilution solutions.

Example 26

Method of Immunorosetting Using Uni-Sep Tubes

A negative selection protocol for immunorosetting cells from whole peripheral blood using centrifugation in a Uni-Sep tube containing a filter disc and Ficoll Hypaque is set out below.

1. Add 50 µL antibody composition per mL of whole peripheral blood.
2. Incubate 20 minutes at room temperature.
3. Add 4 mL of Ficoll Hypaque to empty Uni-Sep tube and centrifuge it through the filter disc.
4. Dilute sample with an equal volume of phosphate buffered saline (PBS)+2% fetal bovine serum (FBS) and mix gently.
5. Gently pour the diluted sample into the Uni-Sep tube.
6. Centrifuge for 20 minutes at 1200×g, room temperature, with the brake off.
7. Pour off the enriched cells.
8. Wash enriched cells with 5–10X volume of PBS=2% FBS.

Note: For enrichment of monocytes and other adherent cells, add 1 mM EDTA to the sample of whole blood and to all wash/dilution solutions.

Example 27

Enrichment of CD8+ T Cells—Immunorosetting Using Dendreon Tubes or Standard Falcon V-bottom Centrifuge Tubes This example compares the enrichment of CD8+ T cells from whole peripheral blood using the methods described in Example 2 and 23. A T cell enrichment cocktail of tetrameric antibody complexes containing antibodies against CD4, CD16, CD19, CD36, and CD56 was prepared. The results, shown in Table 21, demonstrate that the cell separation efficiency was equivalent in the two different types of tubes.

Example 28

Enrichment of T Cells—Immunorosetting Using Vacutainer CPT or Standard Falcon V-Bottom Centrifuge Tubes This example demonstrates the enrichment of T cells from whole peripheral blood using the methods described in Examples 2 and 24. A T cell enrichment cocktail of tetrameric antibody complexes containing antibodies against CD16, CD19, CD36, and CD56 was prepared. The results, shown in Table 22, demonstrate that the cell separation efficiency was equivalent in the two different types of tubes.

Example 29

Enrichment of B Cells—Immunorosetting Using Uni-Sep Tubes or Standard Falcon V-Bottom Centrifuge Tubes This example demonstrates the enrichment of B cells from whole peripheral blood using the methods described in Examples 2 and 26. A B cell enrichment cocktail of tetrameric antibody complexes containing antibodies against CD2, CD3, CD16, CD36, and CD56 was prepared. The results, shown in Table 23, demonstrate that the method of the invention can be performed in either type of tube. The recovery of CD19+ cells was higher with the standard tube.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Antibodies used in Cell Separation

| Antigen | Antibody | Source |
|---------|----------|--------|
| CCR5 | BLR-7 | R&D, Minneapolis, MN |
| CD2 | 6F10.3 | IMMUNOTECH, Marseille, France |
|  | MT910 | Dako, Carpinteria, CA |
| CD3 | UCHT1 | IMMUNOTECH, Marseille, France |
|  | SK7 | Becton Dickinson Immunocytometry, Mountain View, Calif. |
| CD4 | 13B8.2 | Becton Dickinson Immunocytometry, Mountain View, Calif. |
| CD5 | UCHT2 | Serotec, Raleigh, NC |
| CD8 | B911 | Becton Dickinson Immunocytometry, Mountain View, Calif. |
|  | OKT3 | BioDesigns |
| CD9 | M-L13 | Becton Dickinson Immunocytometry, Mountain View, Calif. |
| CD10 | ALB1 | IMMUNOTECH, Marseille, France |
| CD11b | ICRF44 | Pharmingen, San Diego, CA |
| CD14 | MEM 15 | Exbio, Praha, Czech Republic |
|  | MEM 18 |  |
| CD15 | DU-HL60-3 | Sigma, St. Louis, MO |
| CD16 | MEM 154 | Exbio, Praha, Czech Republic |
|  | 3G8 | IMMUNOTECH, Marseille, France |
|  | NKP15 | Becton Dickinson Immunocytometry, Mountain View, Calif. |
| CD19 | J4.119 | IMMUNOTECH, Marseille, France |
|  | 4G7 | Becton Dickinson Immunocytometry, Mountain View, Calif. |
|  | HD37 | Dako, Carpinteria, CA |
| CD20 | MEM97 | Exbio, Praha, Czech Republic |
|  | L27 | Becton Dickinson Immunocytometry, Mountain View, Calif. |
| CD21 | B-Ly4 | Pharmingen, San Diego, CA |
| CD22 | HIB22 | Pharmingen, San Diego, CA |
| CD24 | 32D 12 | Dr. Steinar Funderud, Institute for Cancer Research, Dept. of Immunology, Oslo, Norway IMMUNOTECH, Marseille, France |
|  | ALB9 |  |
| CD25 | 3G10 | Caltag, Burlingame, CA |
| CD27 | 1A4CD27 | IMMUNOTECH, Marseille, France |
| CD29 | Lia1.2 | IMMUNOTECH, Marseille, France |
| CD33 | D3HL60.251 | IMMUNOTECH, Marseille, France |
| CD34 | 581 | IMMUNOTECH, Marseille, France |
| CD36 | FA6.152 | IMMUNOTECH, Marseille, France |
|  | IVC7 | CLB, Central Laboratory of the Netherlands, Red Cross Blood Transfusion Service |
| CD38 | T16 | IMMUNOTECH, Marseille, France |

TABLE 1-continued

Antibodies used in Cell Separation

| Antigen | Antibody | Source |
|---|---|---|
| CD41 | PI1.64 | Kaplan, 5th International Workshop on Human Leukocyte Differentiation Antigens |
| | SZ22 | IMMUNOTECH, Marseille, France |
| CD42a | BebI | Becton Dickinson Immunocytometry, Mountain View, Calif. |
| CD45 | J33 | IMMUNOTECH, Marseille, France |
| | MEM28 | Exbio, Praha, Czech Republic |
| CD45RA | 8D2.2 | Craig et al. 1994, StemCell Technologies, Vancouver, Canada |
| | L48 | Becton Dickinson Immunocytometry, Mountain View, Calif. |
| CD45RO | UCHL1 | Dako, Carpinteria, CA |
| CD56 | T199 | IMMUNOTECH, Marseille, France |
| | MY31 | Becton Dickinson Immunocytometry, Mountain View, Calif. |
| CD66e | CLB/gran10 | CLB, Central Laboratory of the Netherlands, Red Cross Blood Transfusion Service |
| CD66b | B13.9 | CLB, Central Laboratory of the Netherlands, Red Cross Blood Transfusion Service |
| | 80H3 | IMMUNOTECH, Marseille, France |
| CD69 | L78 | BD Biosciences, San Jose, CA |
| CD71 | My29 | Zymed Laboratories, San Francisco, CA |
| CD72 | J4-117 | Becton Dickinson Immunocytometry, Mountain View, Calif. |
| CD124 | S456C9 | IMMUNOTECH, Marseille, France |
| HLADR | IMMU357.12 | IMMUNOTECH, Marseille, France |
| IgA1 | NiF2 | IMMUNOTECH, Marseille, France |
| IgE | G7-18 | Pharmingen, San Diego, CA |
| IgG | 8A4 | IMMUNOTECH, Marseille, France |
| TCRαβ | WT31 | BD Biosciences, San Jose, CA |
| TCRγδ | Immu510 | IMMUNOTECH, Marseille, France |

TABLE 2

Immunorosetting Cocktails of Antibodies for Negative Selection of Human Cells T Cell Enrichment
Anti-
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Resting T Cell Enrichment
Anti-
HLA-DR and/or CD25, CD69
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
γδ T Cell Enrichment
Anti-
αβTCR
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
αβT Cell Enrichment
Anti-
γδTCR
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
CD4+ T Cell Enrichment
Anti-
CD8
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9

TABLE 2-continued

Immunorosetting Cocktails of Antibodies for Negative Selection of Human Cells Naïve CD4+ T Cell Enrichment
Anti-
CD8
CD45RO and/or CD29
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Memory CD4+ T Cell Enrichment
Anti-
CD8
CD45RA
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Resting CD4+ T Cell Enrichment
Anti-
CD8
HLA-DR and/or CD25, CD69
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
CD4+ αβT Cell Enrichment
Anti-
γδTCR
CD8
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
TH1 CD4+ T Cell Enrichment
Anti-
CD8
CD124
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
TH2 CD4+ T Cell Enrichment
Anti-
CD8
CCR5
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
CD8+ T Cell Enrichment
Anti-
CD4
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Naïve CD8+ T Cell Enrichment
Anti-
CD4
CD45RO and/or CD29
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Memory CD8+ T Cell Enrichment
Anti-
CD4
CD45RA
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
Resting CD8+ T Cell Enrichment
Anti-
CD4
HLA-DR and/or CD25, CD69, CD27
CD16 and/or CD66b, CD11b, CD15

TABLE 2-continued

Immunorosetting Cocktails of Antibodies
for Negative Selection of Human Cells

CD19 and/or CD20, CD21, CD22, CD24, Ig, CD72
CD36 and/or CD14
and optionally anti-CD33, CD56, IgE, CD41, CD9
CD8+ αβT Cell Enrichment
Anti-
γδTCR
CD4
CD16 and/or CD66b, CD11b, CD15
CD19 and/or CD20, CD21, CD22, CD24, Ig, CD72
CD36 and/or CD14
and optionally anti-CD33, CD56, IgE, CD41, CD9
B Cell Enrichment
Anti-
CD2 and/or CD3, both CD4 and CD8
CD16 and/or CD66b, CD11b, CD15
CD36 and/or CD14
and optionally anti-CD33, CD56, CD41
NK Cell Enrichment
Anti-
CD3
CD66b and/or CD15
CD19 and/or CD20, CD21, CD22, CD24,CD72
CD36 and/or CD14
and optionally anti-CD33, CD4, IgE, CD41, CD9
Monocyte Enrichment
Anti-
CD2 and/or CD3, CD5
CD19 and/or CD20, CD21, CD22, CD24, CD72
CD66b and/or CD16
and optionally anti-CD8, CD56
Dendritic Cell Enrichment
Anti-
CD3
CD14
CD16
CD19
CD34
CD56
CD66b
Basophil Enrichment
Anti-
CD2
CD3
CD14
CD15
CD16
CD19
CD24
CD34
CD36
CD56
CD45RA
Progenitor Enrichment
Anti-
CD2 and/or CD3
CD16 and/or CD66b
CD19 and/or CD24
CD14
and optionally anti- CD56, CD10, CD45RA, CD38, CD36, CD33,
CD71, CD72, CD9
Erythroid Progenitor Enrichment
Anti-
CD2 and/or CD3
CD16 and/or CD66b
CD19 and/or CD24
CD14
CD45RA
CD33
CD10
and optionally anti- CD56
Myeloid Progenitor Enrichment
Anti-
CD2 and/or CD3
CD16 and/or CD66b
CD19 and/or CD24
CD14

TABLE 2-continued

Immunorosetting Cocktails of Antibodies
for Negative Selection of Human Cells

CD71
CD10
and optionally anti- CD56
Megakaryocyte Progenitor Enrichment
Anti-
CD2 and/or CD3
CD16 and/or CD66b
CD19 and/or CD24
CD14
CD45RA
CD10
and optionally anti- CD56
Epithelial Tumor Cell Enrichment
Anti-
CD45
CD66b
and optionally CD36, CD2, CD3, CD14, CD16, CD19, CD38, CD56,
CD66e

TABLE 3

Antibodies Recognizing Non-Hematopoietic
Antigens Expressed on Epithelial Tumor Cells

| Specificity | Antibody | Antigen | Supplier/Developer |
|---|---|---|---|
| Epithelial cell markers | BerEp4 | ESA, (Epithelial Specific Antigen) (also known as HEA) | DAKO |
| | HEA125 | ESA | Serotec, Cymbus, Pierce, RDI, Biodesign |
| | VU-1D9 | ESA | Cymbus |
| | GP1.4 | EMA, (Epithelial Membrane Antigen)(also known as PEM/Episialin, a sialomucin) | IMMUNOTECH, Marseille, France |
| | VU-4H5 | EMA | Neomarkers |
| | MC.5 | EMA | Biogenex, also Biodesign |
| | B24.1 | EMA | Biomeda |
| | E29 | EMA | DAKO |
| | H11 | EGFR | DAKO |
| | RAR9941 | epithelial glycoprotein | Baxter, Germany |
| | RAR9948 | epithelial glycoprotein | Baxter, Germany |
| Carcinoma (breast, cervical, ovarian, lung, endometrial) | CU-18 | BCA 225 (Breast carcinoma associated antigen) | ID Labs |
| Carcinoma | 115D8 | Carcinoma associated antigen | Biogenex, Biodesign |
| Adenocarcinomas | B72.3 | TAG-72 (Tumour associated glycoprotein) | ID Labs, Biogenex, Signet |
| Adenocarcinomas, mammary & lung carcinomas | B6.2 | Unknown, breast cancer marker | Biogenex |
| Breast Carcinoma | 5E11 | unknown, breast carcinoma | STI |
| | 6E7 | unknown, breast carcinoma | STI |
| | H23A | unknown, breast carcinoma | STI |
| | CA27.29 | MAM-6, mucin | Cedarlane |
| | SM-3 | milk mucin core antigen | Cymbus, Biodesign, Imperial Cancer Research Fund |
| | DF3 | CA 15-3 (breast tumour marker) | ID Labs |

TABLE 3-continued

Antibodies Recognizing Non-Hematopoietic Antigens Expressed on Epithelial Tumor Cells

| Specificity | Antibody | Antigen | Supplier/Developer |
|---|---|---|---|
| | 552 | CA 15-3 | Biodesign |
| | 695 | CA 15-3 | Biodesign |
| | RAR9938 | c-erb B2 | Baxter, Germany |
| | C13B5 | c-erb B2 | IMMUNOTECH, Marseille, France, also Biogenex |
| Lung | MOC-1 | Small cell lung carcinoma | ICN Biomed, also Biodesign |
| | MOC-21 | Small cell lung carcinoma | ICN Biomed, also Biodesign |
| | MOC-31 | Small cell lung carcinoma | ICN Biomed, also Biodesign |
| | MOC-32 | Small cell lung carcinoma | ICN Biomed, also Biodesign |
| | MOC-52 | Small cell lung carcinoma | ICN Biomed, also Biodesign |
| | TFS-4 | Small cell lung carcinoma | Biodesign |
| Melanoma | NKI/C3 | Melanoma associated antigen | ICN Biomed, also Biodesign |
| | NKI/M6 | Melanoma associated antigen | Biodesign |
| | PAL-MI | Melanoma associated antigen | ICN Biomed, also Biodesign |
| | HMB45 | Melanoma cells | Biodesign |
| Ovarian tumour | 185 | CA-125 (ovarian tumour marker) | ICN Biomed, also Biodesign |
| | OV-632 | Ovarian cancinoma marker | ICN Biomed, also Biodesign |
| Gastro-Intestinal Cancer | CA 19-9 | GI tumour marker | ICN Biomed, also Biodesign |
| | CA 242 | GI cancer | BioDesign |
| Renal Cell Carcinoma | RC38 | Renal Cell Carcinoma | Biodesign |
| Ewing's Sarcoma | O13 | | Signet |
| Ewing's Sarcoma | CC49 | on human adenocarcinomas | Signet |
| Neuroblastoma | UJ13A | unknown | Hurko and Walsh (1983) Neurology 33:734 |
| | UJ181.4 | unknown | Hurko and Walsh (1983) Neurology 33:734 |
| | UJ223.8 | unknown | Hurko and Walsh (1983) Neurology 33:734 |
| | UJ127.11 | unknown | Hurko and Walsh (1983) Neurology 33:734 |
| | 5.1.H11 | unknown | Hurko and Walsh (1983) Neurology 33:734 |
| | 390,459 | unknown | R.C. Seeger, L. A. Children's Hospital, Calif. |
| | BA-1.2 | unknown | R.C. Seeger, L. A. Children's Hospital, Calif. |
| | HSAN 1.2 | unknown | Reynolds and Smith (1982) Hybridomas in Cancer p235 |

TABLE 4

T Cell Enrichment - Immunorosetting Using Ficoll

| Purity | mean | 95 |
|---|---|---|
| | SD | 4 |
| | n | 19 |
| Recovery | mean | 46 |
| | SD | 12 |
| | n | 19 |

SD = Standard deviation from the mean
Purity = % CD3+ cells
Recovery = Recovery of CD3+ cells

TABLE 5

CD8+ T Cell Enrichment - Immunorosetting Using Ficoll

| Cocktail | n | % Purity ± 1SD | % Recovery ± 1SD |
|---|---|---|---|
| CD4, CD16, CD19, CD36, CD56 | 19 | 76 ± 8 | 44 ± 19 |
| CD4, CD16, CD19, CD36, CD56, IgE | 5 | 81 ± 4 | 45 ± 37* |

SD = Standard Deviation from the mean
Purity = % CD8+ cells
Recovery = % Recovery of CD8+ cells
*n = 4

TABLE 6

CD4+ T Cell Enrichment - Immunorosetting Using Ficoll

| Cocktail | n | % Purity ± 1SD | % Recovery ± 1SD |
|---|---|---|---|
| CD8, CD16, CD19, CD36, CD56 | 19 | 89 ± 4 | 57 ± 22 |
| CD8, CD16, CD19, CD36, CD56, IgE | 7 | 93 ± 3 | 46 ± 10* |

SD = Standard Deviation from the mean
Purity = % CD4+ cells
Recovery = % Recovery of CD4+ cells
*n = 5

TABLE 7

B Cell Enrichment - Immunorosetting Using Ficoll

| Cocktail | n | % Purity ± 1SD | % Recovery ± 1SD |
|---|---|---|---|
| CD2, CD3, CD16, CD36, CD56 | 22 | 72 ± 15 | 61 ± 27 |
| CD2, CD3, CD16, CD36, CD56, IgE | 5 | 88 ± 7 | 43 ± 18 |

SD = Standard Deviation from the mean
Purity = % CD19+ cells
Recovery = % Recovery of CD19+ cells

TABLE 8

NK Cell Enrichment - Immunorosetting Using Ficoll

| Cocktail | n | % Purity ± 1SD | % Recovery ± 1SD |
|---|---|---|---|
| CD3, CD4, CD19, CD66b, CD36 | 15 | 74 ± 10 | 44 ± 19 |
| CD3, CD4, CD19, CD66b, CD36, IgE | 6 | 88 ± 4 | 27 ± 20 |

SD = Standard Deviation from the mean.
Purity = % CD56+ cells
Recovery = % recovery CD56+ cells

TABLE 9

Enrichment of CD34+ cells from Whole Cord Blood - Immunorosetting Using Ficoll

| Cocktail | n | % Purity ± 1SD | % Recovery ± 1SD |
|---|---|---|---|
| Progenitor Enrichment | 15 | 29 ± 9 | 53 ± 29 |
| Debulking | 8 | 5 ± 1 | 45 ± 20 |

Purity = % CD34+ cells
Recovery = % recovery CD34+ cells
SD = Standard Deviation from the mean

TABLE 10

Monocyte Enrichment - Immunorosetting Using Ficoll

| Cocktail | n | % Purity ± 1SD | % Recovery ± 1SD |
|---|---|---|---|
| CD2, CD3, CD19, CD56, CD66b | 8 | 71 ± 7 | 63 ± 28 |
| CD2, CD3, CD19, CD56, CD66b, CD8 | 5 | 76 ± 1.5 | 65 ± 28 |
| CD2, CD3, CD19, CD56, CD66b, IgE | 6 | 77 ± 4 | 58 ± 24 |
| CD2, CD3, CD19, CD56, CD66b, IgE, CD8 | 4 | 76 ± 3 | 64 ± 26 |
| CD2, CD3, CD19, CD56, CD66b, CD16 | 1 | 76 | 64 |
| CD2, CD3, CD19, CD56, CD66b, CD20 | 1 | 73 | 41 |

Purity = % Purity CD14+ cells
Recovery = % Recovery CD14+ cells

TABLE 11

Antibody Composition of Tumor Enrichment Cocktails

| Cocktail | Antibodies in Cocktail |
|---|---|
| CD45 alone | CD45 |
| CD45 and CD66b | CD45, CD66b |
| CD45, CD66b and CD36 | CD45, CD66b, CD36 |
| Extensive cocktail | CD45, CD2, CD16, CD19, CD36, CD38, CD66b |

TABLE 12

Enrichment of CAMA Breast Cancer Cells from Whole Blood

| | Starting frequency (CAMA) | | | | | | | | |
|---|---|---|---|---|---|---|---|---|---|
| | $1/10^3$ | $1/10^4$ | $1/10^5$ | $1/10^3$ | $1/10^4$ | $1/10^5$ | $1/10^3$ | $1/10^4$ | $1/10^5$ |
| | % Purity of CAMA Cells | | | Log Enrichment of CAMA Cells | | | % Recovery of CAMA Cells | | |
| Enriched | | | | | | | | | |
| CD45 alone | 4 ± 2 (n = 4) | 5 ± 2 (n = 7) | 0.5 ± 0.4 (n = 3) | 1.4 ± 0.3 (n = 4) | 2.2 ± 0.3 (n = 7) | 2.3 ± 0.4 (n = 3) | 10 ± 3 (n = 4) | 26 ± 7 (n = 5) | 55 ± 36 (n = 2) |
| CD45 and 66b | 27 ± 4 (n = 6) | 3.2 ± 0.6 (n = 6) | 0.5 ± 0.1 (n = 5) | 2.4 ± 0.1 (n = 6) | 2.5 ± 0.1 (n = 6) | 2.7 ± 0.1 (n = 5) | 15 ± 2 (n = 6) | 12 ± 1 (n = 5) | 22 ± 4 (n = 5) |
| Extensive Cocktail | 65 ± 8 (n = 9) | 26 ± 8 (n = 9) | 3 ± 1 (n = 6) | 2.8 ± 0.1 (n = 9) | 3.2 ± 0.2 (n = 9) | 3.2 ± 0.3 (n = 6) | 38 ± 8 (n = 7) | 49 ± 14 (n = 5) | 33 ± 7 (n = 5) |

TABLE 13

The Effects of Anti-CD36 Antibody in the Epithelial Tumour Enrichment Cocktail

| Cocktail | % Purity CAMA Cells | % Recovery CAMA Cells | Log Enrichment CAMA cells |
|---|---|---|---|
| none - Ficoll alone | 0.6 | 20 | 0.6 |
| CD45, CD66b | 58 | 11 | 2.6 |
| CD45, CD66b, CD36 | 77 | 18 | 2.7 |
| Extensive Cocktail | 90 | 17 | 2.8 |

TABLE 14

T Cell Enrichment - Immunorosetting Using Ficoll

| | n | Cocktail with CD14 ± 1SD | Cocktail with CD36 ± 1SD |
|---|---|---|---|
| Purity | 3 | 80 ± 10 | 94 ± 5 |
| Recovery | 3 | 56 ± 12 | 42 ± 10 |

SD = Standard Deviation from the mean
Purity = % Purity CD3+ cells
Recovery = % Recovery CD3+ cells

TABLE 15

Immunorosetting Using Hetastarch/Iodixanol Mixture

| Cell Type Enriched | Purity | | | Recovery | | |
|---|---|---|---|---|---|---|
| | mean | SD | n | mean | SD | n |
| T cells | 95% | 3% | 3 | 61% | 9% | 3 |
| CD4+ cells | 89% | 5% | 2 | 64% | 5% | 2 |
| CD8+ cells | 80% | 8% | 2 | 43% | 1% | 2 |
| B cells | 84% | 8% | 5 | 58% | 26% | 5 |
| NK cells | 80% | 15% | 4 | 50% | 23% | 4 |

SD = Standard Deviation from the mean
Purity = % Purity desired cell type (T cells = CD3+ cells, CD4+ cells, CD8+ cells, B cells = CD19+ cells, NK cells = CD56+ cells)
Recovery = % Recovery of desired cells

TABLE 16

Immunorosetting Using Different Layering Media
B Cell Enrichment

| Media | Ficoll | Percoll | Iodixanol |
|---|---|---|---|
| Sample 1 (in triplicate) | | | |
| Purity ± 1SE | 82 ± 2.9 | 81 ± 1.4 | 86 ± 2.7 |
| Recovery ± 1SE | 78 ± 6.0 | 110 ± 3 | 104 ± 10 |
| Sample 2 (in triplicate) | | | |
| Purity ± 1SE | 71 ± 1.2 | 77 ± 1.5 | 81 ± 2.4 |
| Recovery ± 1SE | 49 ± 8 | 78 ± 3 | 64 ± 1 |

SE = Standard Error of the mean
Purity = % Purity of CD19+ cells
Recovery = % Recovery of CD19+ cells

TABLE 17

Purging of Breast Carcinoma Cells Using Immunorosetting

| | Sample 1 | Sample 2 |
|---|---|---|
| Log depletion of CAMA cells | 1.4, 1.4 | 1.1, 1.0 |

TABLE 18

Removal of Granulocytes from Stored Whole Peripheral Blood

| | Immunorosetting | Ficoll alone |
|---|---|---|
| % Granulocytes in light density fraction | 1.1, 1.4, 0.7, 0.4 | 20.9, 18.0 |

Immunorosetting = Method outlined in Example 2, with depletion cocktail containing anti-CD66b
Ficoll alone = Standard Ficoll density separation without immunorosetting

TABLE 19

Examples of Red Cell Aggregating Agents

| Compound | Product Name | Supplier |
|---|---|---|
| Dextran | Dextran | Pharmacia Corporation, North Peapak, NJ |
| Hetastarch | Hespan | Biotime, Berkely, CA |
| Penta starch | Pentaspan | Bristol Myers Squibb Pharma Co. New York, NY |
| Polysucrose | Ficoll | Pharmacia Corporation, North Peapack, NJ |
| Methycellulose | Methocel | Sigma, St. Louis, NO |

TABLE 20

Specialized Containers for the Density Separation or Selective Sedimentation of Cells Vacutainer CPT Supplier: Becton-Dickinson
Location: Franklin Lakes, NJ
Cat No: 362753
Description: evacuated blood collection tube containing an anti-coagulant (sodium Heparin in this case) with a Ficoll Hypaque density fluid and a thixotropic polyester gel barrier which separates the two liquids.

TABLE 20-continued

Specialized Containers for the Density Separation or Selective Sedimentation of Cells Uni-Sep Distributor: Accurate Chemical and Scientific Corporation
Location: Westbury NY
Producer: NovaMed Ltd.
Location: Jerusalem, Israel
Cat No.: NVU-03
Description: plastic centrifuge tube containing a plastic filter disk, called "separation device", partway up the tube. Available containing a buoyant density solution or unfilled. Unfilled tubes must first be centrifuged with a buoyant density medium to fill them, prior to layering on the blood.

Dendreon Tubes and Containers

Supplier: Dendreon
Location: Seattle WA 50 mL Dendreon Tube

Description: standard 50 mL centrifuge tube with a funnel-shaped insert with a central orifice. The tube is partially filled with a buoyant density medium to a level above the insert. "During centrifugation, cells of high density migrate through the density solution and roll down the slope of the insert into the lower compartment where they collect in the pellet. After centrifugation, the cells at the interface are collected by inverting the centrifugation tube. During inversion, an air-lock established tat the orifice due to the surface tension of the density medium. This air-lock is sufficiently strong to retain the cells in the lower compartment of the tube and to prevent the mixing of the cells from the pellet with those from the interface during collection." (typed verbatim from "Cell Separation Methods and Applications, Eds. Diether Recktenwald, AmCell Corporation, Sunnyvale, CA, and Andreas Radbruch, Deutsches Rheuma-Forschungszentrum Berlin, Berlin c. 1998).

Clinical device called DACS ® SC or DACS ™ 300
Buoyant Density Solution 60 (BDS60) Stem Cell Enrichment Device Supplier: Charter Medical, Winston-Salem, NC
Description: A sealed cylindrical container with in-put and exit ports with a funnel-shaped insert with a central orifice. The container is partially filled with a buoyant density medium to a level above the insert. The device consists of a two-chamber separation container with two ports and a filtered air vent. The device is sold as a product containing a buoyant density solution and also includes three tubing sets for transfer of samples to and from the separation container. The cell suspension is layered over the buoyant density solution and centrifuged to separate cells based upon their relative buoyant densities. After centrifugation, desired cells (CD34+ cells) are found in the interface in the upper chamber whereas cells with a higher density sediment to the bottom in the lower chamber. The upper and lower chambers are separated by an airlock that prevents drainage of the pellet when the device is inverted to recover the desired cells after centrifugation. D Przepiorka et al., Cytotherapy (1999) Vol. 2, 111–117.

TABLE 21

CD8+ T Cell Enrichment - Immunorosetting Using
Dendreon Tubes or Standard Falcon Centrifuge Tubes

| Dendreon | Dendreon | Standard | Standard |
|---|---|---|---|
| purity | recovery | purity | recovery |
| 49 | 88 | 49 | 87 |

Purity = % CD8+ cells
Recovery = % Recovery of CD8+ cells

TABLE 22

T Cell Enrichment - Immunorosetting Using Vacutainer CPT or Standard Falcon Centrifuge Tubes

|  | CPT Purity | CPT Recovery | Standard Purity | Standard Recovery |
|---|---|---|---|---|
| Mean | 93 | 62 | 96 | 50 |
| SD | 4 | 18 | 2 | 8 | n = 6
SD = standard deviation from the mean
Purity = % CD3+ cells
Recovery = % Recovery of CD3+ cells

TABLE 23

B Cell Enrichment - Immunorosetting Using Uni-Sep Tubes or Standard Falcon Centrifuge Tubes

| Uni-Sep purity | Uni-Sep recovery | Standard Purity | Standard recovery |
|---|---|---|---|
| 98 | 45 | 97 | 97 |

Purity = % CD19+ cells
Recovery = % Recovery of CD19+ cells

FULL CITATIONS FOR REFERENCES REFERRED TO IN THE SPECIFICATION

1. Braun et al., N. Engl. J. Med., 342:525–533.
2. Brenner, M. B., Trowbridge, I. S., Strominger, J. L., 1985, Cell 40:183–190.
3. De Lau, W. B., Van Loon, A. E., Heije, K., Valerio, D., Bast, B. J., 1989, J. Immunol. Methods, 117:1–8.
4. deWynter, E. A. et al., 1975, Stem Cells, Vol. 13:524–532.
5. Firat et al., 1988, Bone Marrow Transplantation, Vol. 21:933–938.
6. Glennie, M. J., McBride, H. M., Worth, A. T., Stevenson, G. T., 1987, J. Immunol., 139:2367–2375.
7. Holliger, P., Prospero, T., Winter, G., 1993, Proc. Natl. Acad. Sci. USA, 90:6444–6448.
8. Karawajew, L., Micheel, B., Behrsing, O., Gaestel, M., 1987, J. Immunol. Methods 96:265–270.
9. Kostelny, S. A., Cole, M. S., Tso, J. Y., 1992, J. Immunol. 148:1547–1553.
10. Kohler and Milstein, 1975, Nature 256, 495–497.
11. Milstein, C., Cuello, A. C., 1983, Nature, 305:537–540.
12. Nolan, O., Kennedy, O. R., 1990, Biochem. Biophys. Acta, 1040:1–11.
13. Perez et al., 1985, Nature 316:354.
14. Przepiorka, D., et al. 1999, Cytotherapy. 2:111–117.
15. Rheinnecker et al., 1996, J. Immunol. 157:2989–2997.
16. Roboredo, N. M. et al., 2000, Bone Marrow Transplantation. 26:1263–1270
17. Shpall, E. J., et al. 1994, J. of Clinical Oncology 12:28–36.
18. Slaper-Cortenbach, Ineke C. M., et al., 1990, Exp. Hematol. 18:49–54.
19. Staerz & Bevan, 1986, PNAS (USA) 83: 1453.
20. Staerz & Bevan, 1986, Immunology Today, 7:241.
21. Staerz et al., 1985, Nature, 314:628.
22. Thomas, T. E., 1994, Cancer Research, Therapy and Control 4(2): 119–128.
23. Van Dijk, J. et al., 1989, Int. J. Cancer 44:738–743.
24. Vaughan et al., 1990, Proc. Am. Soc. Clin. Oncol. 9:9.
25. Winter, G., Milstein, C., 1991, Nature, 349:293–299.

We claim:

1. A negative selection method for enriching and recovering desired cells in a sample containing the desired cells, erythrocytes and undesired cells comprising:
   (1) contacting the sample with an agglutinating agent and an antibody composition comprising (a) at least one antibody that is specific for an antigen on the undesired cells linked, either directly or indirectly, to (b) at least one antibody that binds to the erythrocytes, under conditions to allow immunorosettes of the undesired cells and the erythrocytes to form; and
   (2) separating the immunorosettes from the sample to obtain a sample enriched in the desired cells.

2. A method according to claim 1 wherein the agglutinating agent is dextran.

3. A method according to claim 1 wherein the agglutinating agent is hetastarch.

4. A method according to claim 1 wherein antibody (b) comprises anti-glycophorin A antibody.

5. A method according to claim 1 wherein the immunorosettes are separated in step (2) in a container.

6. A method according to claim 5 wherein the container contains an insert which forms a barrier between the immunorosettes and the sample.

7. A method according to claim 6 wherein the insert is a gel, plug, screen or funnel.

8. A method according to claim 5 wherein the container is an evacuated blood collection tube containing anti-coagulant, buoyant density medium and a thixotropic gel.

9. A method according to claim 1 wherein the antibody composition comprises tetrameric antibody complexes comprising (a) an antibody that is specific for the antigen on the undesired cells; and (b) an antibody that binds to the erythrocytes; and (c) two antibodies that bind to the Fc fragment of the antibodies defined in (a) and (b), wherein the antibodies in (a) and (b) are of the same animal species and the antibodies in (c) are of a different animal species from the antibodies in (a) and (b).

10. A composition for separating nucleated cells in a sample comprising (1) (a) at least one antibody that is specific for an antigen on the nucleated cells linked, either directly or indirectly to (b) at least one antibody that binds to erythrocytes and (2) an agglutinating agent.

11. An antibody composition according to claim 10 wherein the agglutinating agent comprises dextran.

12. An antibody composition according to claim 10 wherein the agglutinating agent comprises hetastarch.

13. An antibody composition according to claim 10 wherein antibody (b) comprises anti-glycophorin A antibody.

14. An antibody composition according to claim 10 wherein the antibody composition comprises tetrameric antibody complexes comprising (a) an antibody that is specific for the antigen on the undesired cells; and (b) an antibody that binds to the erythrocytes; and (c) two antibodies that bind to the Fc fragment of the antibodies defined in (a) and (b), wherein the antibodies in (a) and (b) are of the same animal species and the antibodies in (c) are of a different animal species from the antibodies in (a) and (b).

* * * * *